(12) United States Patent
Jeong et al.

(10) Patent No.: US 12,150,768 B2
(45) Date of Patent: Nov. 26, 2024

(54) ELECTRONIC DEVICE AND ELECTRODE IN THE SAME

(71) Applicant: Samsung Electronics Co., Ltd., Suwon-si (KR)

(72) Inventors: Injo Jeong, Suwon-si (KR); Hyunguk Yoo, Suwon-si (KR); Seongwook Jo, Suwon-si (KR); Younghyun Kim, Suwon-si (KR); Suho Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 716 days.

(21) Appl. No.: 17/370,373

(22) Filed: Jul. 8, 2021

(65) Prior Publication Data
US 2022/0022794 A1   Jan. 27, 2022

(30) Foreign Application Priority Data

Jul. 22, 2020   (KR) .......................... 10-2020-0091246

(51) Int. Cl.
*A61B 5/265*    (2021.01)
*A61B 5/00*     (2006.01)
(Continued)

(52) U.S. Cl.
CPC ............ *A61B 5/265* (2021.01); *A61B 5/6898* (2013.01); *H01B 1/02* (2013.01); *H05K 5/0017* (2013.01);
(Continued)

(58) Field of Classification Search
CPC .............. A61B 5/265; A61B 5/6898; A61B 2562/0215; A61B 2562/04; H01B 1/02; H05K 5/0017; H05K 5/03; H05K 7/1427
See application file for complete search history.

(56) References Cited

U.S. PATENT DOCUMENTS

| 10,238,312 B2 | 3/2019 | Eom et al. |
| 2008/0246025 A1* | 10/2008 | Nomura ................. H10K 10/82 |
| | | 257/E29.295 |

(Continued)

FOREIGN PATENT DOCUMENTS

| EP | 2367292 B1 | 5/2016 |
| KR | 10-2012-0078639 A | 7/2012 |
| WO | 2019/177769 A1 | 9/2019 |

OTHER PUBLICATIONS

International Search Report dated Oct. 13, 2021, issued in International Application No. PCT/KR2021/008500.
(Continued)

*Primary Examiner* — Linda C Dvorak
*Assistant Examiner* — Abigail Bock
(74) *Attorney, Agent, or Firm* — Jefferson IP Law, LLP

(57) ABSTRACT

An electronic device is provided. The electronic device includes a housing, a display viewed through at least a portion of a front surface of the housing, a rear cover disposed on a rear surface of the housing, a first electrode disposed on a lateral surface of the housing, and second and third electrodes disposed at different positions on the rear cover. The first electrode, the second electrode, and the third electrode may include a conductive material that is a compound containing titanium (Ti), aluminum (Al), chromium (Cr), silicon (Si), carbon (C), and nitrogen (N).

20 Claims, 15 Drawing Sheets

(51) Int. Cl.
  *H01B 1/02*   (2006.01)
  *H05K 5/00*   (2006.01)
  *H05K 5/03*   (2006.01)
  *H05K 7/14*   (2006.01)
(52) U.S. Cl.
  CPC ............ *H05K 5/03* (2013.01); *H05K 7/1427* (2013.01); *A61B 2562/0215* (2017.08); *A61B 2562/04* (2013.01)

(56) References Cited

U.S. PATENT DOCUMENTS

| | | |
|---|---|---|
| 2011/0221688 A1 | 9/2011 | Byun et al. |
| 2012/0179055 A1 | 7/2012 | Tamil et al. |
| 2014/0044944 A1 | 2/2014 | Cha et al. |
| 2014/0221850 A1 | 8/2014 | Farringdon et al. |
| 2015/0164349 A1 | 6/2015 | Gopalakrishnan et al. |
| 2015/0305632 A1 | 10/2015 | Najarian et al. |
| 2019/0090806 A1 | 3/2019 | Clavelle et al. |
| 2019/0101870 A1* | 4/2019 | Pandya .................. A61B 5/339 |
| 2019/0274563 A1* | 9/2019 | Soli ........................ G06F 9/453 |

OTHER PUBLICATIONS

European Search Report dated Sep. 28, 2023, issued in European Application No. 21847262.9.

* cited by examiner (a)

(b)

ELECTRONIC DEVICE AND ELECTRODE IN THE SAME

CROSS-REFERENCE TO RELATED APPLICATION(S)

This application is based on and claims priority under 35 U.S.C. § 119(a) of a Korean patent application number 10-2020-0091246, filed on Jul. 22, 2020, in the Korean Intellectual Property Office, the disclosure of which is incorporated by reference herein in its entirety.

BACKGROUND

1. Field

The disclosure relates to an electronic device and an electrode included in the same.

2. Description of Related Art

As interest in health increases, electronic devices are being developed to provide functions capable of measuring user's biometric information. For example, wearable electronic devices are equipped with various sensors capable of measuring user's biometric information.

The user's biometric information may be measured by recognizing an electrical signal flowing through a user body or applying an electrical signal to a user body. In order to recognize or applying an electrical signal, the electronic device may include an electrode to contact a user body.

The electrode included in the electronic device may be directly exposed to an external environment. Therefore, the electrode should be able to withstand changes in the external environment (e.g., changes in temperature, changes in humidity, or changes in light).

In order to remove noise generated while measuring a bioelectrical signal, filters such as a high pass filter (HPF) and a low pass filter (LPF) are used, but there may be limitations in removing such noise. In order to improve the quality of the measured bio-signal, it is necessary to use an electrode having a constant surface potential distribution of resistance on its surface and having a low resistance.

In addition, the electrode included in the electronic device is highly likely to be damaged when exposed to the external environment. If the electrode is damaged, the measurement quality of the bio-signal may be degraded.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, as aspect of the disclosure is to provide an electrode satisfying required surface resistance and durability, and an electronic device including the electrode.

Additional aspects will be set forth in part in the description which follows and, in part, will be apparent from the description, or may be learned by practice of the presented embodiments.

In accordance with an aspect of the disclosure, an electronic device is provided. The electronic device includes a housing, a display viewable through at least a portion of a front surface of the housing, a rear cover disposed on a rear surface of the housing, a first electrode disposed on a lateral surface of the housing, and second and third electrodes disposed at different positions on the rear cover. The first electrode, the second electrode, and the third electrode may include a conductive material that is a compound containing titanium (Ti), aluminum (Al), chromium (Cr), silicon (Si), carbon (C), and nitrogen (N).

In accordance with another aspect of the disclosure, an electrode of an electronic device is provided. The electrode includes a first electrode disposed on a portion of a housing of the electronic device, and second and third electrodes disposed at different positions on a rear cover disposed on a rear surface of the housing. The first electrode, the second electrode, and the third electrode may include a conductive material that is a compound containing titanium (Ti), aluminum (Al), chromium (Cr), silicon (Si), carbon (C), and nitrogen (N).

According to various embodiments of the disclosure, the electrode having excellent durability and low surface resistance resulting in high electrical conductivity can be provided. This electrode not only can maintain its characteristics for a long time even when exposed to the outside of the electronic device because of having excellent durability, but also can accurately measure a bio-signal because of a low resistance.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features and advantages of certain embodiments of the disclosure will be more apparent from the following description taken in conjunction with the accompanying drawings, in which.

The same reference numerals are used to represent the same elements throughout the drawings.

DETAILED DESCRIPTION

The following description with reference to the accompanying drawings is provided to assist in a comprehensive understanding of various embodiments of the disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

Figure 1:
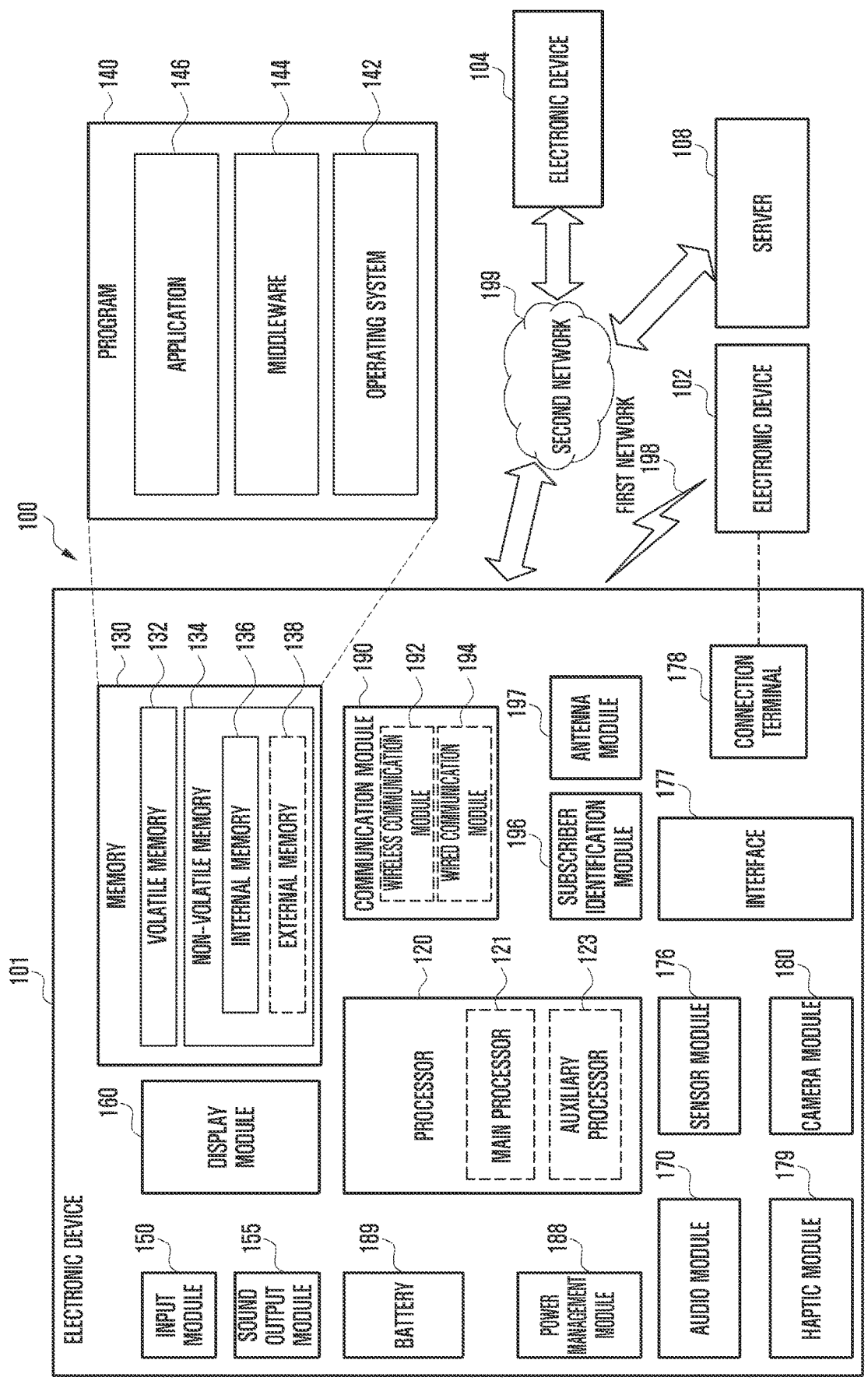
FIG. 1 is a block diagram illustrating an electronic device in a network environment according to an embodiment of the disclosure.

FIG. 1 is a block diagram illustrating an electronic device 101 in a network environment 100 according to an embodiment of the disclosure.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134. The non-volatile memory 134 may include internal memory 136 and external memory 138.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
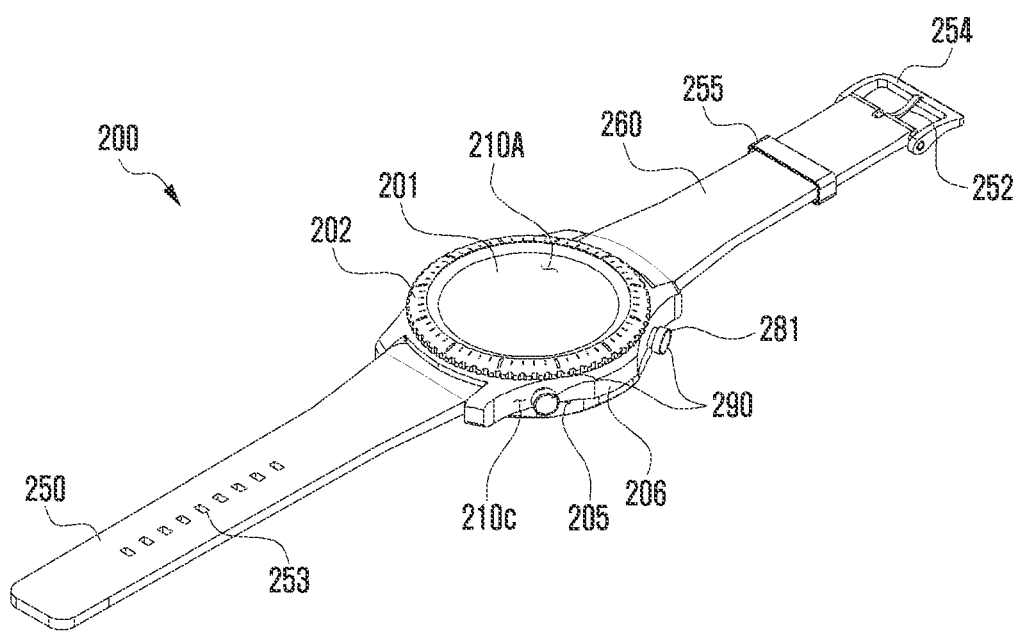
FIG. 2 is a front perspective view illustrating a mobile electronic device according to an embodiment of the disclosure.

FIG. 2 is a front perspective view illustrating a mobile electronic device according to an embodiment of the disclosure.

Figure 3:
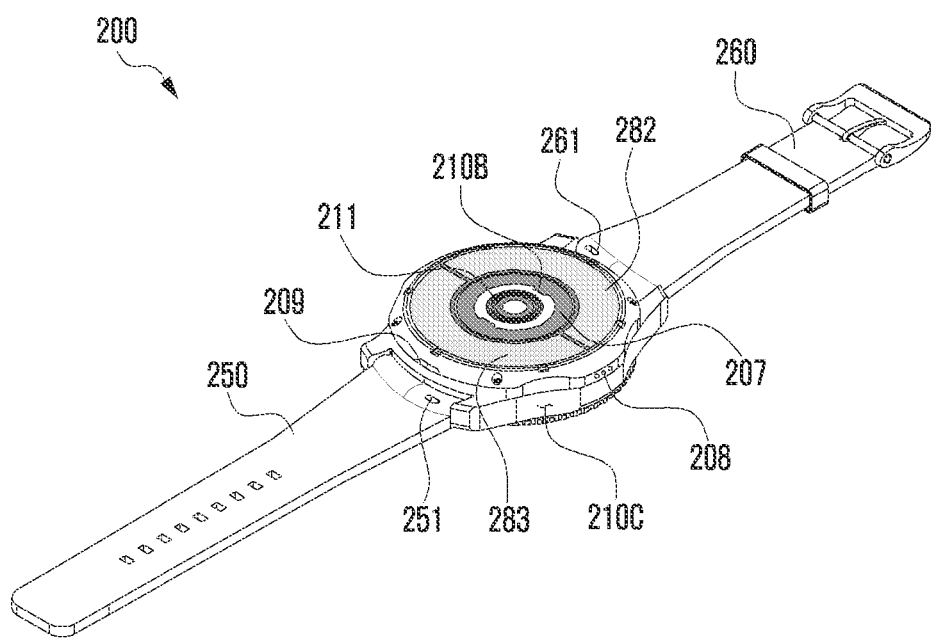
FIG. 3 is a rear perspective view illustrating the electronic device of FIG. 2 according to an embodiment of the disclosure.

FIG. 3 is a rear perspective view illustrating the electronic device of FIG. 2 according to an embodiment of the disclosure.

Figure 4:
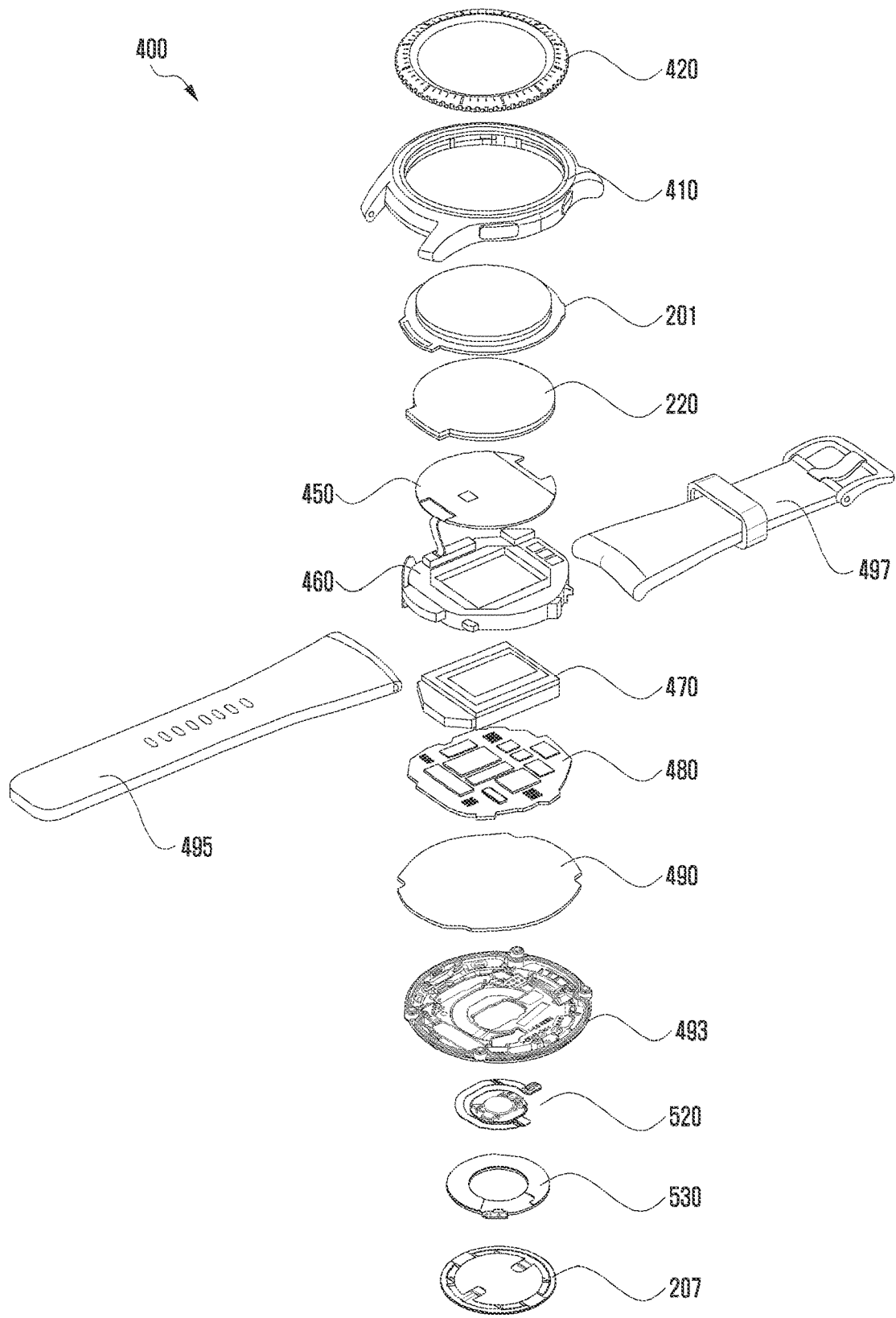
FIG. 4 is an exploded perspective view illustrating the electronic device of FIG. 2 according to an embodiment of the disclosure.

FIG. 4 is an exploded perspective view illustrating the electronic device of FIG. 2 according to an embodiment of the disclosure.

Referring to FIGS. 2 and 3, an electronic device 200 (e.g., the electronic device 101 in FIG. 1) may include a housing 210 having a first surface (or front surface) 210A, a second surface (or rear surface) 210B, and a lateral surface 210C enclosing a space between the first surface 210A and the second surface 210B. In addition, the electronic device 200 may include fastening members 250 and 260 connected to at least a portion of the housing 210 and configured to detachably attach the electronic device 200 to a user's body part (e.g., wrist, ankle, etc.) of a user's body. According to another embodiment of the disclosure (not shown), the housing may refer to a structure forming some of the first surface 210A, the second surface 210B, and the lateral surface 210C. The first surface 210A may be formed at least in part by a substantially transparent front plate 201 (e.g., a polymer plate or a glass plate including various coating layers). The second surface 210B may be formed by a substantially opaque rear cover 207. The rear cover 207 may be formed by coated or colored glass, ceramic, polymer, metal (e.g., aluminum, stainless steel (STS), or magnesium), or a combination of at least two of the above materials. The lateral surface 210C may be formed of a lateral bezel structure 206 (or "lateral member") combined with the front plate 201 and the rear cover 207 and having a metal and/or a polymer. The rear cover 207 and the lateral bezel structure 206 may be integrally formed with each other and have the same material (e.g., a metal material such as aluminum), although other arrangements are possible. The fastening members 250 and 260 may be formed of various materials and shapes. For example, the fastening members 250 and 260 may be formed integrally by woven fabric, leather, rubber, urethane, metal, ceramic, or any combination thereof, or be formed with a plurality of unit links that are flexible with each other.

The electronic device 200 may include at least one of a display 220 (see FIG. 4), audio modules 205 and 208, a sensor module 211, key input devices 202 and 290, and a connector hole 209. At least one (e.g., the key input devices 202 and 290, the connector hole 209, or the sensor module 211) of the above components may be omitted. The electronic device 200 may further include other components not shown.

The display 220 may be exposed through a portion of the front plate 201. The display 220 may have a shape corresponding to the shape of the front plate 201, and may have various shapes such as a circle, an oval, or a polygon. The display 220 may be disposed adjacent to or combined with a touch sensing circuit, a pressure sensor capable of measuring the intensity (or pressure) of a touch, and/or a fingerprint sensor.

The audio modules 205 and 208 may include a microphone hole 205 and a speaker hole 208. The microphone hole 205 may contain a microphone for obtaining an external sound, and may contain a plurality of microphones to detect a direction of a sound. The speaker hole 208 may be used for an external speaker and a call receiver. The speaker hole 208 and the microphone hole 205 may be implemented as one hole, or a speaker (e.g., a piezo speaker) may be included without the speaker hole 208.

The sensor module 211 may generate an electrical signal or data value corresponding to an internal operating state or external environmental state of the electronic device 200. The sensor module 211 may include a biometric sensor module 211 (e.g., a heart rate monitor (HRM) sensor) disposed on the second surface 210B of the housing 210. The electronic device 200 may further include any other sensor module (not shown) such as a gesture sensor, a gyro sensor, an air pressure sensor, a magnetic sensor, an acceleration sensor, a grip sensor, a color sensor, an infrared (IR) sensor, a biometric sensor, a temperature sensor, a humidity sensor, and/or an illumination sensor.

The key input devices 202 and 290 may include a wheel key 202 disposed on the first surface 210A of the housing 210 and rotatable in at least one direction, and/or a side key button 290 disposed on the lateral surface 210C of the housing 210. The wheel key may have a shape corresponding to the shape of the front plate 201. One or both of the aforementioned key input devices 202 and 290 may be omitted; the key input device(s) that is/are omitted may be implemented in another form, such as a soft key on the display 220. The connector hole 209 is capable of accommodating a connector (e.g., a USB connector) for transmitting and receiving power and/or data to and from an external electronic device, and may include another connector hole (not shown) capable of accommodating a connector for transmitting and receiving an audio signal to and from an external electronic device. The electronic device 200 may further include a connector cover (not shown) that covers at least a portion of the connector hole 209 to block the inflow of external foreign substances into the connector hole.

The fastening members 250 and 260 may be attached to and detached from at least a portion of the housing 210 through locking members 251 and 261. The fastening members 250 and 260 may have a band or strap shape, and may include one or more of a fixing member 252, fixing member insertion holes 253, a band guide member 254, and a band support ring 255.

The fixing member 252 may be inserted into one of the fixing member insertion holes 253 to fix the housing 210 and the fastening members 250 and 260 to a part (e.g., wrists, ankles, etc.) of the user's body. The band guide member 254 may limit the range of motion of the fixing member 252 inserted into the fixing member insertion hole 253 so that the fastening members 250 and 260 may be in close contact with a part of the user's body. The band support ring 255 may limit the range of motion of the fastening members 250 and 260 in a state where the fixing member 252 is inserted into the fixing member insertion hole 253.

Referring to FIG. 4, an electronic device 400 may include a lateral bezel structure 410, a wheel key 420, the front plate 201, the display 220, a first antenna 450, a support member 460 (e.g., a bracket), a battery 470, a first printed circuit board (PCB) 480, a sealing member 490, a rear plate 493, and fastening members 495 and 497. Some components of the electronic device 400 may be the same as or similar to those of the electronic device 200 shown in FIG. 2 or FIG. 3, so that descriptions thereof are omitted below. The support member 460 is disposed inside the electronic device 400 and may be connected to, or integrated with, the lateral bezel structure 410. The support member 460 may be formed of, for example, a metal material and/or a non-metal (e.g., polymer) material. The support member 460 may be combined with the display 220 at one side thereof and also combined with the first PCB 480 at the other side thereof. A processor, a memory, and/or an interface may be mounted on the first PCB 480. The processor may include one or more of a CPU, an application processor (AP), a graphic processing unit (GPU), a sensor processor, or a communication processor (CP).

The memory may include a volatile memory or a non-volatile memory. The interface may include, for example, a high definition multimedia interface (HDMI), a universal serial bus (USB) interface, a secure digital (SD) card interface, and/or an audio interface. The interface may electrically or physically connect the electronic device 400 with an external electronic device and may include a USB connector, an SD card/multimedia card (MMC) connector, or an audio connector.

The battery 470 is a device for supplying power to at least one component of the electronic device 400, and may include a non-rechargeable primary battery, a rechargeable secondary battery, or a fuel cell. At least a part of the battery 470 may be disposed on substantially the same plane as the first PCB 480. The battery 470 may be disposed integrally within, or detachably from, the electronic device 400.

The first antenna 450 may be disposed between the display 220 and the support member 460. The first antenna 450 may include a near field communication (NFC) antenna, a wireless charging antenna, and/or a magnetic secure transmission (MST) antenna. For example, the first antenna 450 may perform short-range communication with an external device, wirelessly transmit and receive power required for charging, or transmit a short-range communication signal or a magnetic-based signal including payment data. In An antenna structure may also be formed by a part or combination of the lateral bezel structure 410 and/or the support member 460.

The sealing member 490 may be positioned between the lateral bezel structure 410 and the rear plate 493. The sealing member 490 may be configured to block moisture and foreign matter flowing into a space surrounded by the lateral bezel structure 410 and the rear plate 493 from the outside.

A second PCB 520 (e.g., a PCB, a flexible PCB (FPCB), or rigid-flexible PCB (RFPCB)) and a coil 530 for wireless charging may be disposed between the rear plate 493 and the rear cover 207. The second PCB 520 may be electrically connected to the first PCB 480 through a hole formed in the rear plate 493. The wireless charging coil 530 may be disposed to surround the outer periphery of the second PCB 520.

The electronic device (e.g., the electronic device 101 in FIG. 1, the electronic device 200 in FIG. 2) may include the housing 210, the display 220 viewed through at least a portion of the first surface 210A (or front surface) of the housing 210, and the rear cover 207 disposed on the second surface 210B (or rear surface) of the housing 210.

The electronic device may include a plurality of electrodes exposed to the outside so as to be in contact with a user's body. For example, the electrode may include a first electrode 281, a second electrode 282, and a third electrode 283. The number of electrodes included in the electronic device may be variously changed. Hereinafter, a total of three electrodes of the electronic device will be described, but the number of electrodes included in the electronic device may be one, two, four, or more.

At least one of the electrodes 281, 282, and 283 of the electronic device 200 may be disposed at least one of a position of the key input device 202 or 290, a position of the lateral bezel structure 206, a position of the display 220, or a position of the housing 210.

For example, the first electrode 281 may be disposed on the lateral surface 210C of the electronic device housing 210. As shown in FIG. 2, the first electrode 281 may be formed on at least one of the buttons 290 disposed on the lateral surface 210C of the housing 210. The button 290 disposed on the lateral surface 210C of the housing 210 may be a physical button that is pressed by the user's body and moves forward and backward with respect to the housing 210, or a touch button that recognizes contact with the user's body. The button 290 may be formed of a conductive substance, and the first electrode 281 may be formed on the button 290.

As shown in FIG. 3, the second electrode 282 and the third electrode 283 may be disposed on the rear cover 207 forming the rear surface 210B of the electronic device housing 210. The second electrode 282 and the third electrode 283 may be disposed at different positions on the rear cover 207. The second electrode 282 and the third electrode 283 may be electrically isolated from each other on the rear cover 207.

At least one of the first electrode 281, the second electrode 282, and the third electrode 283 may be an electrode that contacts the user's skin and is capable of measuring an electrical signal according to the user's physical activity. For example, at least one of the first electrode 281, the second electrode 282, and the third electrode 283 may contact the user's skin and measure an electrical signal according to the user's heartbeat.

Figure 5A:
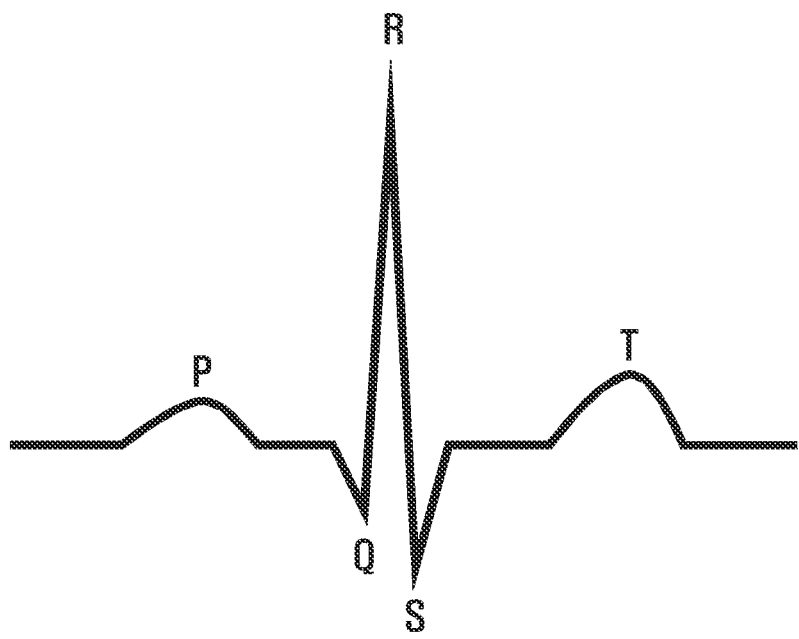
FIG. 5A illustrates an electrocardiogram waveform according to an embodiment of the disclosure.
Figure 5B:
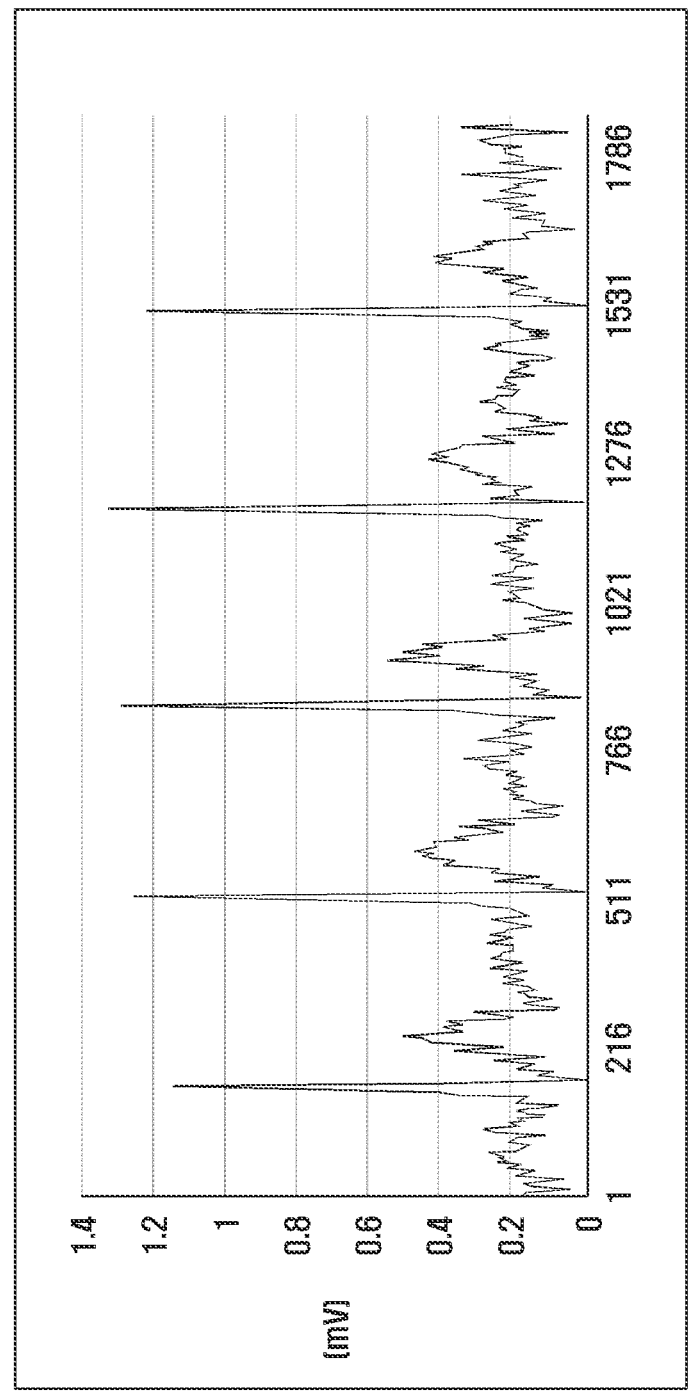
FIG. 5B is a graph illustrating an electrocardiogram waveform measured by an electronic device according to an embodiment of the disclosure.

FIG. 5A illustrates an electrocardiogram waveform, and FIG. 5B is a graph illustrating an electrocardiogram waveform measured by an electronic device according to various embodiments of the disclosure.

Referring to FIGS. 5A and 5B, an electrode (e.g., the first electrode 281, the second electrode 282, or the third electrode 283 in FIGS. 2 and 3) may be in contact with a user's body and detect a user's bioelectrical signal. An electronic device (e.g., the electronic device 400 in FIG. 4) may obtain information about the user's body from the bioelectrical signal measured through the electrode. The body information measured through the electrode may be information related to a heartbeat. For example, the electrode may measure a user's electrocardiogram (ECG) signal. The heartbeat may be identified through an electrical signal. When the heart muscle contracts or relaxes, the action potential created by the heartbeat spreads from the heart to the whole body. When electrodes are attached to different body parts, it is possible to obtain a potential difference of electric currents caused by contraction or relaxation of the heart muscle. For example, the ECG measurement may be performed by detecting a microscopic bioelectrical signal from the skin when the heart muscle is depolarized at each heartbeat. The ECG signal may be plotted as a potential difference graph over time. As shown in FIG. 5A, the ECG signal may be represented as an ECG waveform. The ECG waveform may be composed of P, Q, R, S, and T waves. The P wave is a waveform indicating the start of atrial depolarization, the QRS waves are waveforms indicating the ventricular depolarization, and the T wave is a waveform indicating normal repolarization of the ventricle. FIG. 5A shows an ideal ECG waveform for a unit heartbeat, and FIG. 5B may be a plot of an actual potential difference over time measured for a continuous heartbeat.

Because the ECG signal is recorded by measuring the potential difference over time, the quality of the ECG signal may be determined depending on how well the potential difference of the electrical signal according to contraction and relaxation of the heart muscle is followed. The potential difference may be affected by a difference in a material forming the electrode that is in contact with the user's body. The material forming the electrode has a unique oxidation reduction potential (or equilibrium oxidation reduction potential) for each material. The oxidation-reduction potential refers to a potential value for maintaining an equilibrium state in which an oxidation-reduction reaction does not occur because of the same oxidation and reduction rates. If the electrodes disposed at different parts of the user's body for ECG measurement have different materials, a difference in the oxidation-reduction potential may be reflected in the ECG signal as it is. The potential difference due to the difference in the materials forming the electrodes may be mainly reflected in a low potential difference portion (e.g., 0~0.2 mV portion in FIG. 5B) in the ECG signal. In addition, when the potential difference is calculated through the electrodes disposed at different parts of the user's body, the user's body acts as a resistance, and the resistance value may be reflected in the ECG signal. Therefore, in order to reduce the resistance caused by the user's body, a signal transmission path of the electrode may be formed to be short. In addition, in order to accurately measure the potential difference according to the bioelectric signal, the electrode should be able to measure sensitive changes in the bioelectric signal, which may be related to the electrical conductivity of the electrode.

In order to measure the ECG signal of a specified quality through the electrode included in the electronic device, a plurality of electrodes contacting the user's body may be formed of the same material having high electric conductivity.

When the electronic device according to various embodiments of the disclosure is a wrist-worn electronic device, the rear cover 207 disposed on the rear surface 210B of the housing 210 may be in contact with the user's wrist in a state where the electronic device is worn. The second electrode 282 and the third electrode 283 may be disposed on the rear cover 207, so that the second and third electrodes 282 and 283 may be in contact with the user's wrist while the user is wearing the electronic device. In this case, a finger of a hand without the electronic device may be brought into contact with the first electrode 281 disposed on the lateral surface 210C of the electronic device housing 210. For example, when the electronic device is worn, the first electrode 281 may be in contact with the finger of one hand of the user, and the second and third electrodes 282 and 283 may be in contact with the wrist of the other hand of the user. It is therefore possible to measure the ECG signal through a potential difference between the electrodes disposed at different parts of the body.

The first electrode 281, the second electrode 282, and the third electrode 283 may include the same conductive material. As described above, when the same conductive material is used for the electrodes, the potential difference of the material itself is reduced and thus it is possible to measure the ECG signal of a specified quality. The conductive material included in the electrode may have high electrical conductivity so as to detect fine current changes in skin well. The electrode included in the electronic device should not change its characteristics even by external factors such as temperature, humidity, and light, and should be resistant to impact or corrosion because of being exposed to the outside of the electronic device. In addition, the electrode that is in contact with the user's body may be formed of a hypoallergenic material with little skin irritation. For example, the conductive material used for the electrode of the electronic device may have high electrical conductivity and high durability. For example, the electrode included in the electronic device may be an electrode having a Mohs hardness (MOHS) of 5 or more.

Figure 6A:
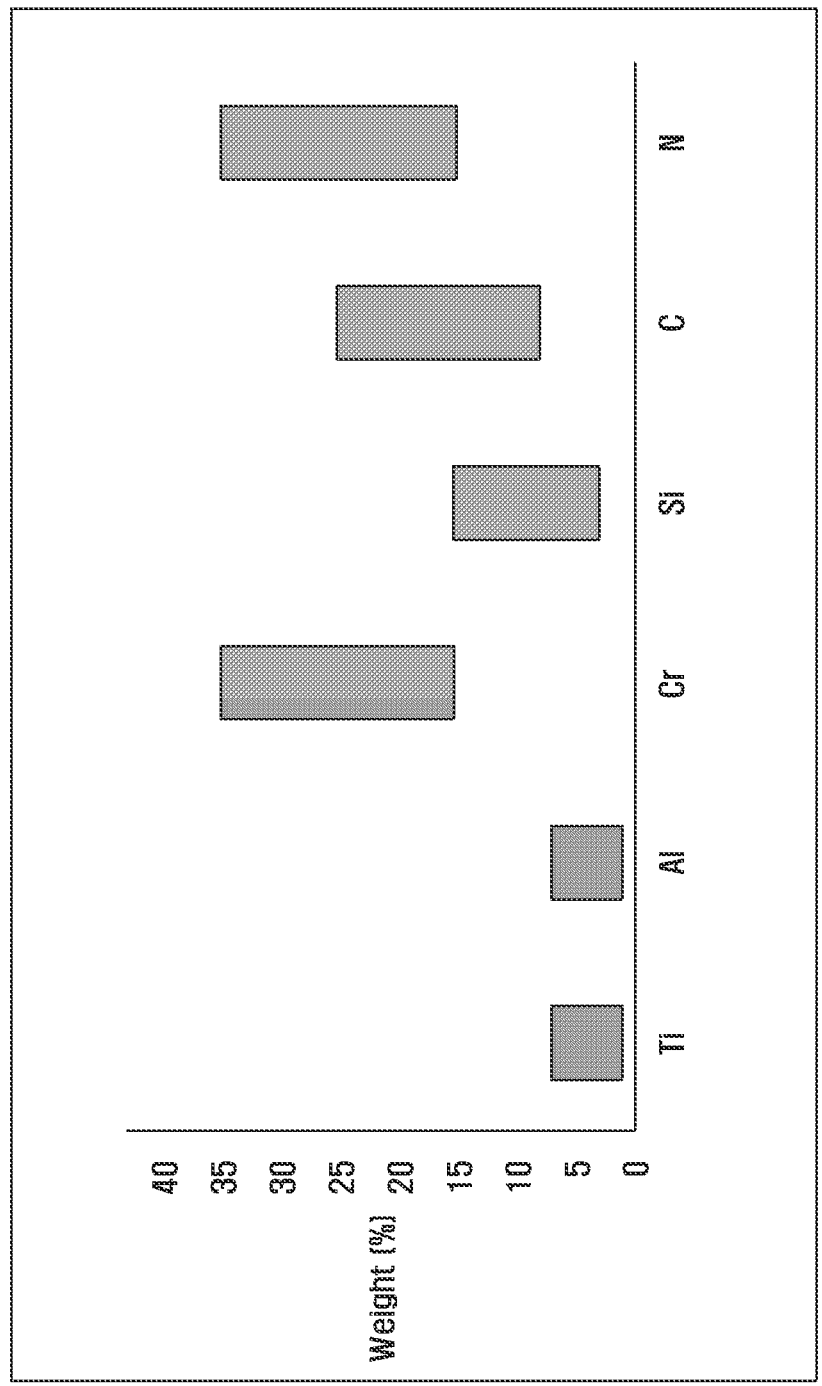
FIG. 6A is a diagram illustrating a composition of a conductive material included in an electrode according to an embodiment of the disclosure.

FIG. 6A is a diagram illustrating a composition of a conductive material included in an electrode according to an embodiment of the disclosure.

Referring to FIG. 6A, the first electrode 281, the second electrode 282, and the third electrode 283 may include at least one material having high durability and high electric conductivity.

The first electrode 281, the second electrode 282, and the third electrode 283 may include at least one of an oxide-based material, a nitride-based material, and/or a carbide-based material. For example, oxide-based materials may include transparent materials such as indium tin oxide (ITO), tin oxide (SnO), zinc oxide (ZnO), and fluorine-doped tin oxide (FTO), and/or opaque materials such as titanium dioxide (TiO$_2$). Nitride-based materials may include chromium nitride (CrN), chromium carbon-nitride (CrCN), chromium silicon carbon nitride (CrSiCN), titanium nitride (TiN), titanium carbon nitride (TiCN), chromium boron carbon nitride (CrBCN), chromium boron silicon carbon nitride (CrBSiCN), chromium titanium carbon nitride (CrTiCN), chromium titanium silicon carbon nitride (CrTiSiCN), chromium aluminum carbon nitride (CrAlCN), and chromium aluminum silicon carbon nitride (CrAlSiCN). Carbide-based materials may include tungsten carbide (WC) and titanium carbide (TiC).

The first electrode 281, the second electrode 282, and the third electrode 283 may use TiAlCrSiCN (hereinafter referred to as "conductive material"), which is a compound containing titanium (Ti), aluminum (Al), chromium (Cr), silicon (Si), carbon (C) and nitrogen (N) as conductive materials. The conductive material may have high durability as well as high electric conductivity. A CrSiCN material containing chromium, silicon, carbon and nitrogen has high electrical conductivity and high durability, so it may be advantageous for surface coating. Adding titanium to the CrSiCN material can improve electrical properties (e.g., electric conductivity), and adding aluminum can improve heat resistance and thereby improve durability.

Referring to FIG. 6A, the composition of the conductive material according to various embodiments of the disclosure may include titanium (Ti) of about 1 to 7% by weight, aluminum (Al) of about 1 to 7% by weight, chromium (Cr) of about 15 to 35% by weight, silicon (Si) of about 3 to 15% by weight, carbon (C) of about 8 to 25% by weight, and nitrogen (N) of about 15 to 35% by weight. This composition may be a composition of a conductive material in consideration of high electrical conductivity (e.g., surface resistance within 500 ohm) and high durability (e.g., Mohs hardness of 5 or more). The composition shown in FIG. 6A and described above does not limit the composition of the conductive material of the disclosure, and may be variously changed within a range apparent to a person skilled in the art. Compositions of the electrodes (e.g., the first electrode 281, the second electrode 282, and the third electrode 283) may be different.

The above-described composition may be adjusted depending on the positions where the electrodes are disposed. For example, an electrode disposed at a position that is in continuous contact with the user's body may be adjusted in composition to increase durability, and an electrode disposed at a position that is in intermittent contact with the user's body may be adjusted in composition to increase electrical conductivity. If the content of titanium increases, the electrical conductivity of the conductive material may increase, but the strength and hardness of the conductive material may decrease, and the frictional force of the surface may increase. The composition of titanium may be about 1 to 7% by weight. If the content of aluminum increases, the color becomes dark and the heat resistance may be enhanced. However, if the aluminum composition exceeds a certain threshold, the conductive material may have a red color. The composition of aluminum may be about 1 to 7% by weight. Chromium may improve the corrosion resistance of the conductive material, but may increase the reflectivity of the conductive material. The composition of chromium may be about 15 to 35% by weight. Silicon may improve the hardness of the conductive material by smoothing the surface, but if the composition of silicon exceeds a certain threshold, the strength of the conductive material may decrease. The composition of silicon may be about 3 to 15% by weight. Carbon may darken the color of the conductive material. The composition of carbon may be about 8 to 25% by weight. The conductive material containing a certain ratio of nitrogen may have improved hardness. The composition of nitrogen may be about 15 to 35% by weight.

The composition of the conductive material may be adjusted by regulating several parameters in deposition equipment. Sputter or e-beam may be used as the deposition equipment. In general, since the number of targets in a deposition equipment chamber is limited, a target may be formed by using several materials alone or in combination, and a composition ratio may be adjusted by regulating several parameters in each chamber.

Titanium (Ti), aluminum (Al), chromium (Cr), and silicon (Si) may be used alone or in combination to form a target. For example, when titanium and aluminum are mixed to form a target, the target composition ratio, that is, the ratio of titanium to aluminum may be a ratio of about 30~50% to about 50~70%. Chromium and silicon may be used alone or in combination to form a target. When chromium and silicon are mixed to form a target, the ratio of chromium to silicon may be a ratio of about 40~60% to about 40~60%. Carbon may be used alone to form a target. Gaseous carbon may also be used. In this case, carbon can be obtained from acetylene ($C_2H_2$). In case of nitrogen, gaseous nitrogen may be used.

The composition of the conductive material may be adjusted through the power of the target. The power of the target may be, for example, about 2 to 5 kW in case of titanium or aluminum, about 1 to 6 kW in case of chromium, and about 2 to 8 kW in case of silicon. In case of a target formed of a mixture of chromium and silicon, a power of about 4 to 8 kW may be used. In case of a target formed of carbon, a power of about 3 to 6 kW may be used. When a gaseous carbon is used, the gas flow may be about 10 to 60 sccm, and when a gaseous nitrogen is used, the gas flow may be 30 to 400 sccm. Here, sccm is a unit of gas flow, which is an abbreviation of standard cubic centimeter per minute and may mean the amount of gas contained in the volume of 1 cc per minute in the standard temperature and pressure (STP) state.

TABLE 1

|  | Surface Resistance (Ω/sq) | Resistance Fluctuation (ΔΩ · cm) | Surface Hardness (MOHS) |
| --- | --- | --- | --- |
| $1^{st}$ Material | 240 | 13 | 5 |
| $2^{nd}$ Material | 82 | 2.1 | 5 |
| $3^{rd}$ Material | 68 | 1.9 | 5 |

Table 1 shows a comparison of the surface resistance, resistance fluctuation, and surface hardness between TiAlCrSiCN containing titanium (Ti), aluminum (Al), chromium (Cr), silicon (Si), carbon (C) and nitrogen (N) and CrSiCN containing chromium (Cr), silicon (Si), carbon (C) and nitrogen (N).

In Table 1, the first material is a compound composed of chromium of about 35%, silicon of about 15%, carbon of about 10%, and nitrogen of about 40%. The second material is a compound composed of titanium of about 3%, aluminum of about 5%, chromium of about 35%, silicon of about 11%, carbon of about 12%, and nitrogen of about 34%. The third material is a compound composed of titanium of about 6%, aluminum of about 4%, chromium of about 34%, silicon of about 15%, carbon of about 9%, and nitrogen of about 32%. The second material and the third material may be understood as the conductive materials disclosed herein.

In measuring an electrical signal caused by a user's biological activity in contact with the user's skin, it is preferable to use an electrode having a low surface resistance and a low resistance fluctuation. Comparing the first material with the second material and the third material, it can be seen that the surface resistance and resistance fluctuation of the second and third materials are lower than those of the first material. Therefore, compared to the first material, the second and third materials may be advantageous in measuring a bio-signal. In addition, it can be seen that the surface hardness of the second and third materials is Mohs hardness of 5, which is the same as that of the first material.

Figure 6B:
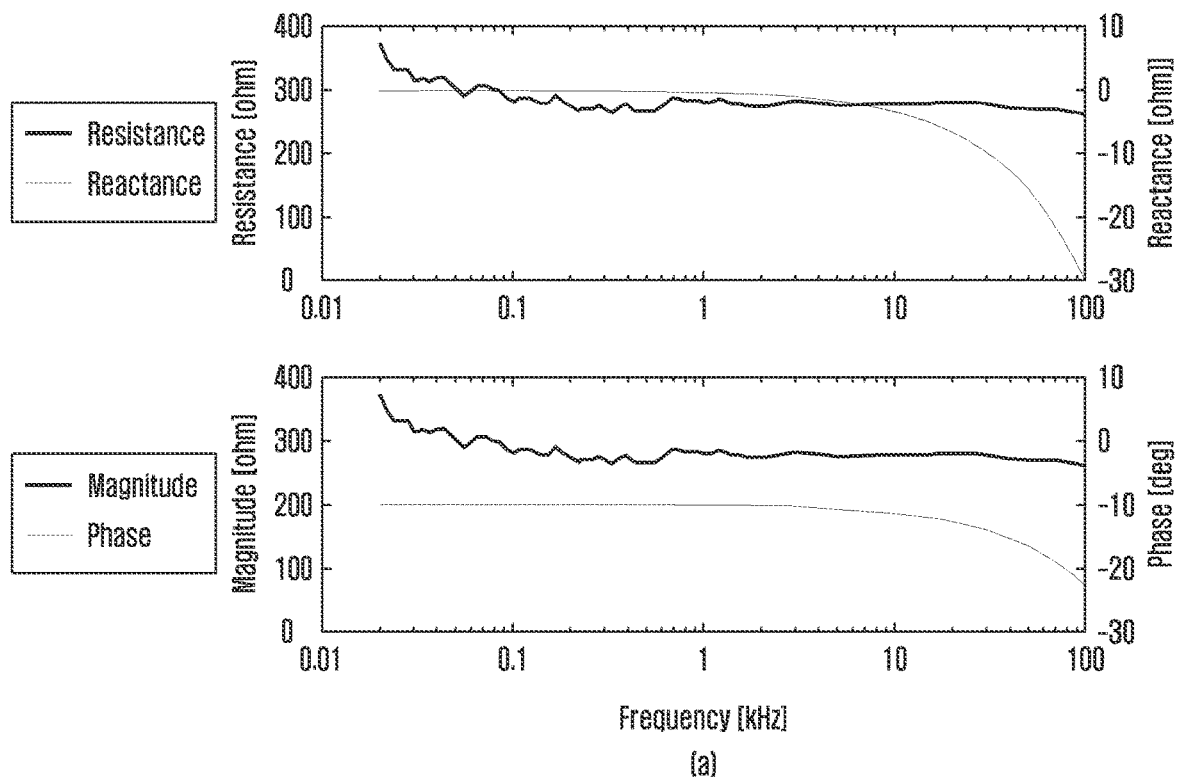
FIG. 6B is a graph illustrating electrical properties of a conductive material according to an embodiment of the disclosure.
Figure 6B:
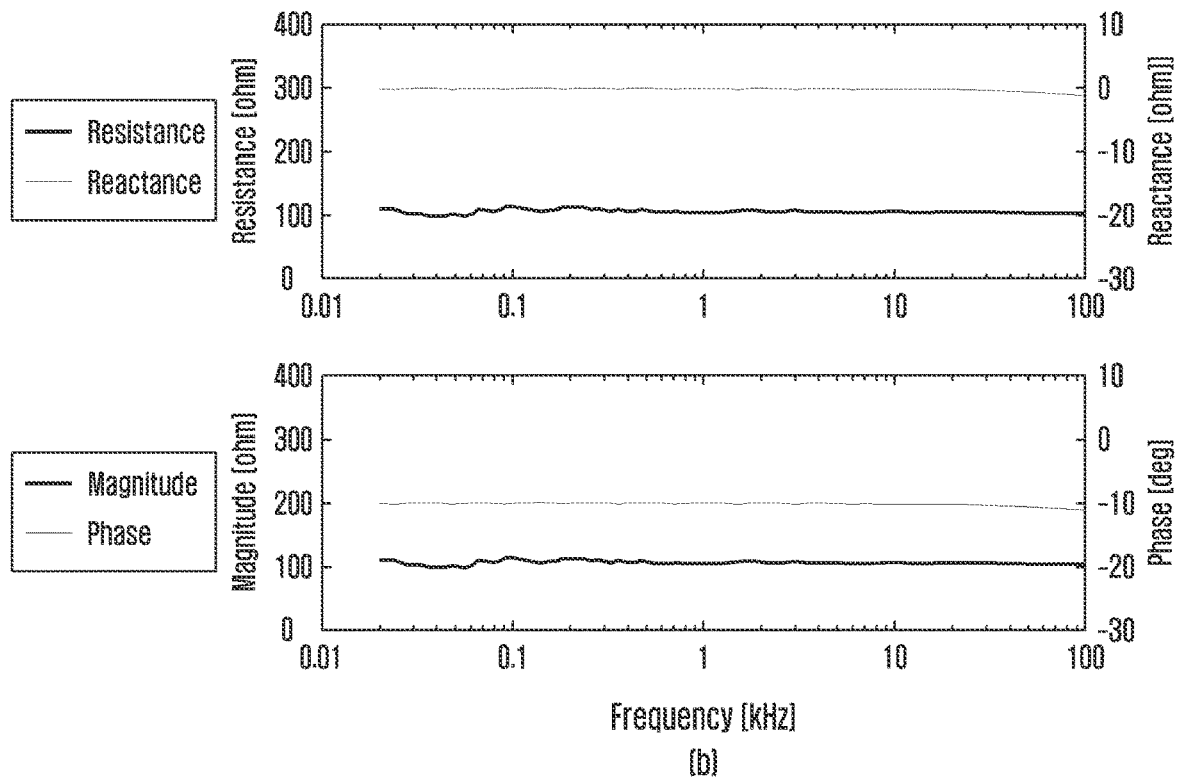

FIG. 6B is a graph illustrating electrical properties of a conductive material according to an embodiment of the disclosure.

Referring to FIG. 6B, a graph (a) shows the electrical properties of a compound according to the related art, which is composed of chromium (Cr), silicon (Si), carbon (C), and nitrogen (N) (hereinafter referred to as "material according to the related art"). In FIG. 6B, a graph (b) shows the electrical properties of a conductive material composed of titanium (Ti), aluminum (Al), chromium (Cr), silicon (Si), carbon (C), and nitrogen (N) described above. Such graphs show the resistance, reactance, and phase of each material according to frequency.

Referring to FIG. 6B, it can be seen that the resistance of the conductive material is lower than that of the material according to the related art in all frequency ranges. Since it is possible to receive a higher quality signal through a material having a lower resistance, the conductive material may be more advantageous in receiving a higher quality signal than the material according to the related art. In addition, it can be seen that the resistance of the material appears differently depending on the frequency, whereas the resistance of the conductive material is maintained at a constant level even with a frequency change. Therefore, the conductive material can perform a more stable measurement.

In case of the conductive material, it can be seen that a phase change of current and voltage at different frequencies is not large, and thus a change in reactance is not large. On the other hand, in case of the material, it can be seen that the phase change of current and voltage appears large at different frequencies, and the change in reactance is also relatively large according to the related art. The conductive material having a small phase change of current and voltage even in different frequency ranges can measure electrical signals more stably than the material having a large phase change according to the related art.

Figure 7A:
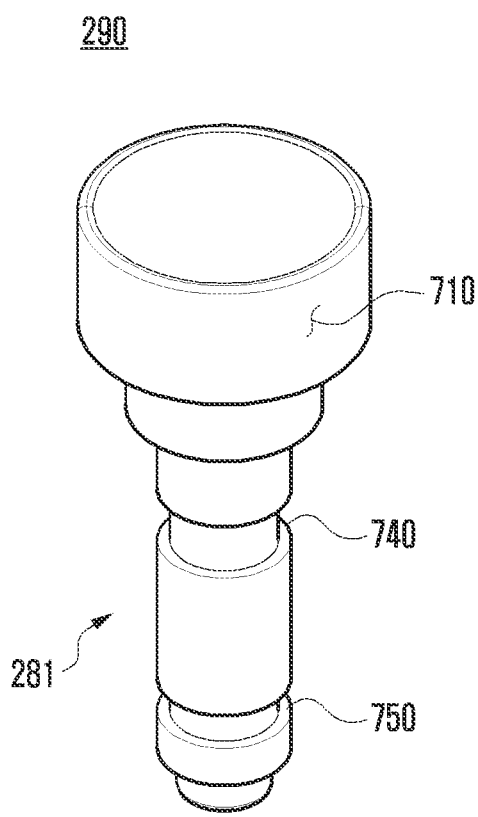
FIGS. 7A, 7B, and 7C are perspective views illustrating a button of an electronic device according to various embodiments of the disclosure.
Figure 7B:
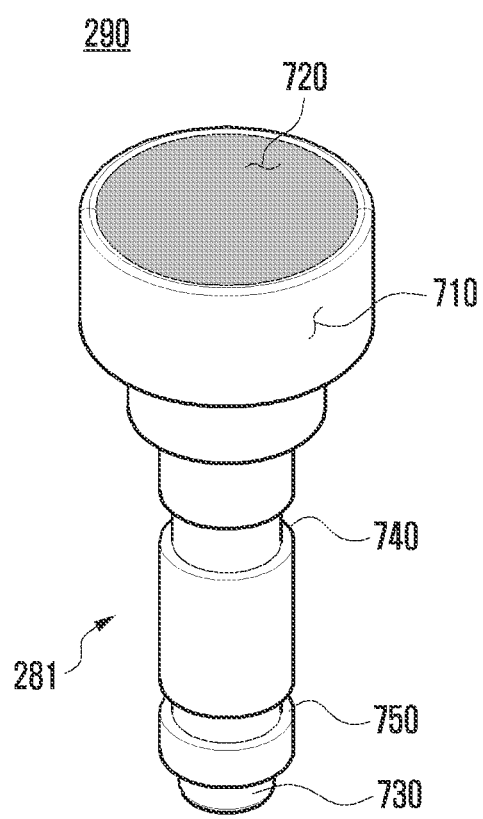

FIGS. 7A-7B are perspective views illustrating a button of an electronic device according to various embodiment of the disclosure.

Referring to FIG. 7A, according to various embodiments, the first electrode 281 may be formed on a button 290 (e.g., the button 290 in FIG. 2) disposed on a lateral surface (e.g., the lateral surface 210C in FIG. 2) of an electronic device housing (e.g., the housing 210 in FIGS. 2 and 3). The button 290 may be formed to be inserted into a hole formed in the housing. The button 290 may include a conductive substance. In order to prevent the button 290 from detaching from the housing, the button 290 may have grooves 740 and 750 or recesses into which O-ring and E-ring are inserted. At least a portion of an outer surface 710 of the button 290 may include a non-conductive material. For example, a portion of the outer surface 710 of the button 290 may be formed of an organic material, a ceramic material, or a combination thereof. When a portion of the lateral surface 210C where the button 290 is positioned includes a conductive substance, at least a portion of the outer surface 710 of the button 290 being in contact with the conductive substance of the lateral surface 210C may include a non-conductive material. As shown in FIG. 7A, an upper surface 720 and a lower surface 730 of the button 290 may not include a non-conductive material.

Figure 7C:
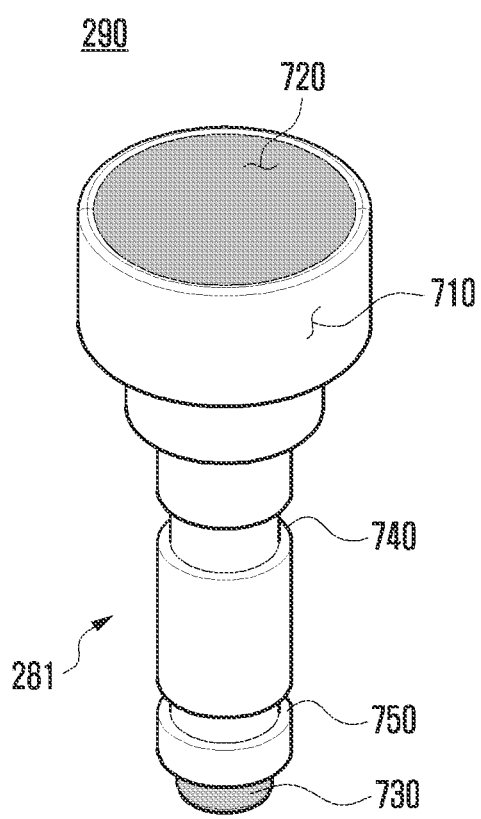

Referring to FIGS. 7B and 7C, the upper surface 720 of the button 290 may be a part to be in contact with the user's body (e.g., user's finger), and the lower surface 730 of the button 290 may be a part being in contact with a terminal installed on a PCB (e.g., the FPCB 520 in FIG. 4). At least one of the upper and lower surfaces 720 and 730 of the button 290 may include the above-described conductive material (TiAlCrSiCN). For example, as shown in FIG. 7B, only the upper surface 720 of the button 290 may include the conductive material, or as shown in FIG. 7C, both the upper surface 720 and the lower surface 730 of the button 290 may include the conductive material. The upper surface 720 of the button 290 including the first electrode 281 may be exposed to the outside of the electronic device. If the upper surface 720 exposed to the outside includes a conductive material, it is possible to reduce a change in characteristics of the first electrode 281 due to external environmental factors because the conductive material has excellent durability and corrosion resistance. If the lower surface 730 of the button 290 being in continuous contact with the terminal of the PCB 520 includes a conductive material having excellent durability, it is possible to reduce fatigue deterioration due to repeated contact.

Figure 8A:
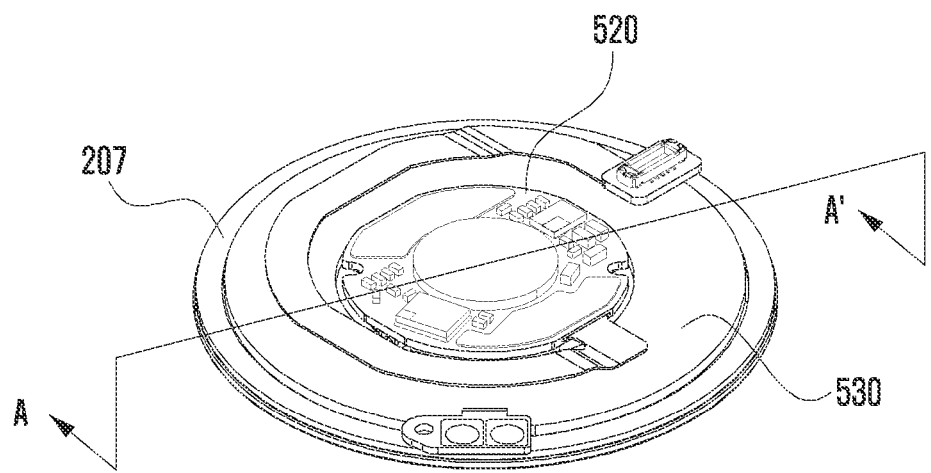
FIG. 8A is a perspective view illustrating a state in which a printed circuit board, a coil for wireless charging, and a rear cover of an electronic device are combined according to an embodiment of the disclosure.

FIG. 8A is a perspective view illustrating a state in which a printed circuit board, a coil for wireless charging, and a rear cover of an electronic device are combined according to an embodiment of the disclosure.

Figure 8B:
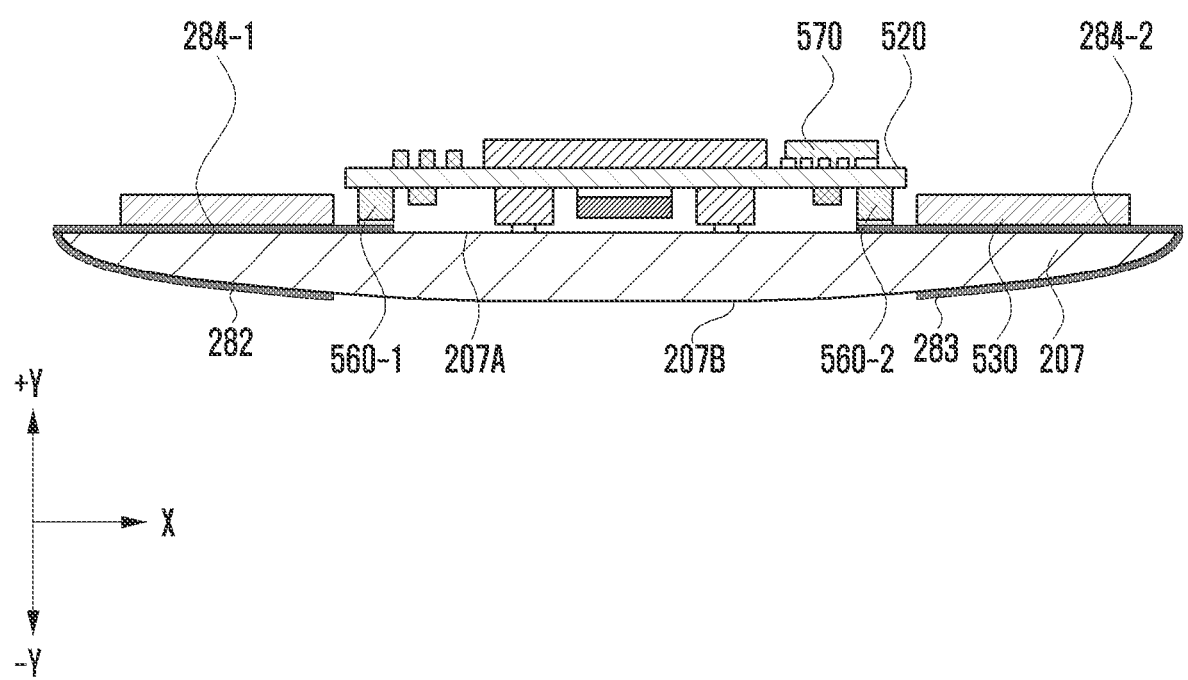
FIG. 8B is a cross-sectional view taken along the line A-A in FIG. 8A according to an embodiment of the disclosure.

FIG. 8B is a cross-sectional view taken along the line A-A in FIG. 8A according to an embodiment of the disclosure.

Referring to FIG. 8A, at least a portion of the rear cover 207 may be formed of a light-transmitting material. The rear cover 207 may have a first surface 207A that substantially faces the PCB 520, and a second surface 207B that is opposite to the first surface 207A.

Referring to FIG. 8B, at least a portion of the second electrode 282 and the third electrode 283 may be substantially disposed on the second surface 207B of the rear cover 207. The second surface 207B of the rear cover 207 may be a surface being in contact with the user's skin while the user is wearing the electronic device. The second electrode 282 and the third electrode 283 disposed on at least a portion of the second surface 207B of the rear cover 207 may contact the user's skin while the user is wearing the electronic device. At least a portion of the second electrode 282 and the third electrode 283 may be deposited on the second surface 207B of the rear cover 207 through various methods. For example, a method such as printing, sputtering deposition, or chemical vapor deposition (CVD) may be used for depositing at least a portion of the second and third electrodes 282 and 283 on the second surface 207B of the rear cover 207. In an embodiment, the second electrode 282 and the third electrode 283 may include the above-described conductive material (TiAlCrSiCN).

A first connection electrode 284-1 and a second connection electrode 284-2 may be substantially disposed on the first surface 207A of the rear cover 207. According to an embodiment of the present disclosure, the first connection electrode 284-1 and the second connection electrode 284-2 may include the above-described conductive material (TiAlCrSiCN). According to another embodiment of the present disclosure, because the first surface 207A of the rear cover 207 is not exposed to the outside of the electronic device, the weight of considering durability may be low in selecting materials of the first and second connection electrodes 284-1 and 284-2 disposed on the first surface 207A. For example, the ratio of materials (e.g., aluminum, chromium) included in the conductive material in consideration of durability may be low. The first and second connection electrodes 284-1 and 284-2 may include, for example, at least one of a conductive paste (e.g., a silver paste, a conductive carbon paste), a conductive film, and a conductive polymer. For example, the conductive paste has an advantage of high electrical conductivity and low process difficulty during surface mounting. The first connection electrode 284-1 may be electrically connected to the second electrode 282, and the second connection electrode 284-2 may be electrically connected to the third electrode 283. Such connection may be made in a region that is not exposed to an external environment after assembly. For example, referring to FIG. 8B, connection may be made on an outer circumferential surface of the rear cover 207. In another example, each of the second and third electrodes 282 and 283 may be extended from the first surface 207A of the rear cover 207 to a portion of the second surface 207B of the rear cover 207 along the outer circumferential surface of the rear cover 207 and then electrically connected to each of the first and second connection electrodes 284-1 and 284-2 disposed on the second surface 207B of the rear cover 207.

The first connection electrode 284-1 and the second connection electrode 284-2 may be electrically connected to a first contact part 560-1 and a second contact part 560-2, respectively, which are disposed on the PCB 520. The first contact part 560-1 and the second contact part 560-2 may be, for example, a gasket, a c-clip, a pogo pin, or a connector. One end of the first contact part 560-1 may be disposed on the PCB 520, and the other end of the first contact part 560-1 may contact the first connection electrode 284-1. Similarly, one end of the second contact part 560-2 may be disposed on the PCB 520, and the other end of the second contact part 560-2 may contact the second connection electrode 284-2. Referring to FIG. 8B, the first contact part 560-1 and the second contact part 560-2 may be formed to extend in a direction from the PCB 520 to the rear cover 207 (e.g., in the −Y direction in FIG. 8B). The second and third electrodes 282 and 283 are electrically connected to the first and second connection electrodes 284-1 and 284-2, respectively, and also the first and second connection electrodes 284-1 and 284-2 are electrically connected to the PCB 520 through the first and second contact parts 560-1 and 560-2, respectively. As a result, the second and third electrodes 282 and 283 may be electrically connected to the PCB 520. A signal processor 570 disposed on the PCB 520 may receive a bioelectrical signal measured through the second and third electrodes 282 and 283.

Figure 9A:
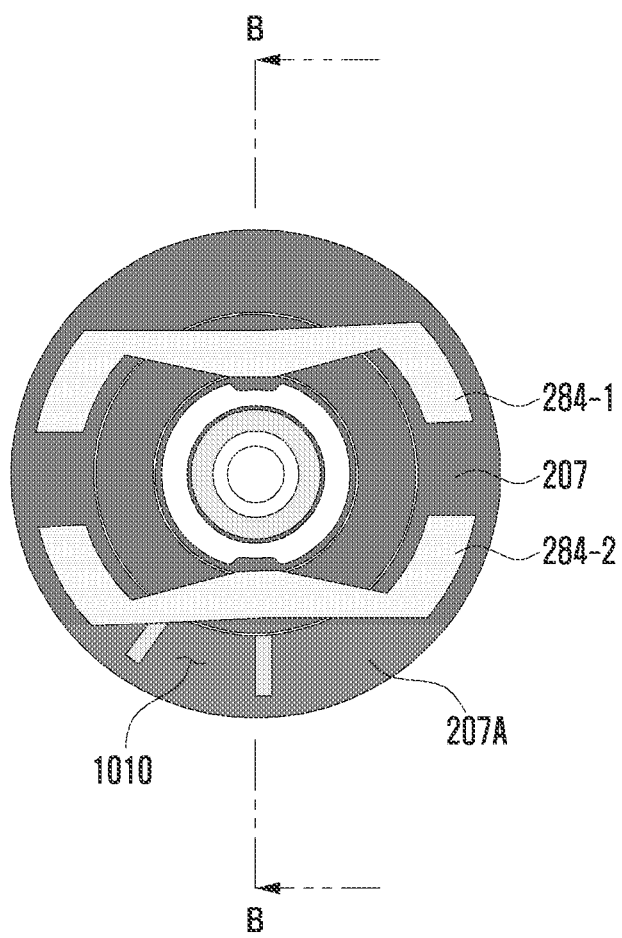
FIG. 9A is a plan view illustrating a rear cover according to an embodiment of the disclosure.

FIG. 9A is a plan view illustrating a rear cover according to an embodiment of the disclosure.

Figure 9B:
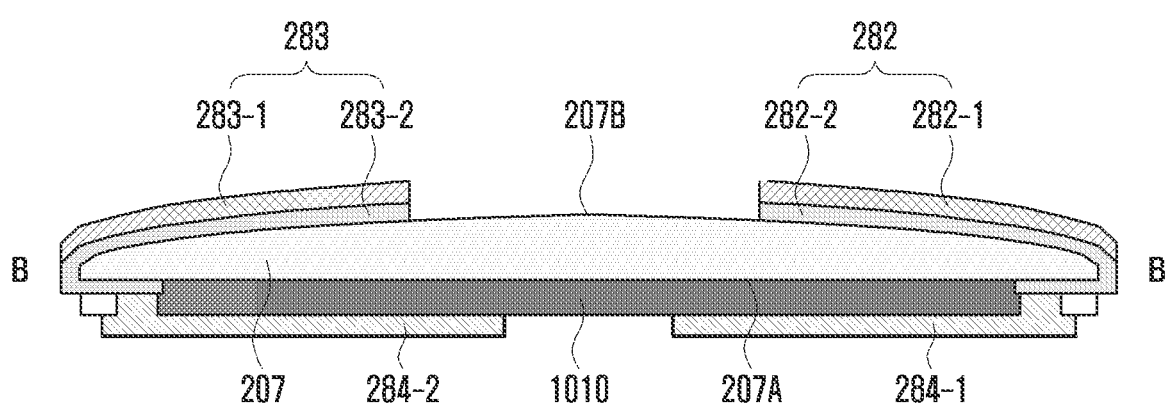
FIG. 9B is a cross-sectional view taken along the line B-B in FIG. 9A according to an embodiment of the disclosure.

FIG. 9B is a cross-sectional view taken along the line B-B in FIG. 9A according to an embodiment of the disclosure.

Referring to FIGS. 9A and 9B, the thickness of the second and third electrodes 282 and 283 shown in FIG. 9B is exaggerated for clarity. The second and third electrodes 282 and 283 are very thin, so an operation difference due to the second and third electrodes 282 and 283 is not visible to the naked eye. For example, the thickness of the second and third electrodes 282 and 283 may be about 1 μm to 100 μm.

Referring to FIGS. 9A and 9B, at least a portion of the first and second connection electrodes 284-1 and 284-2 may be disposed in at least a partial region of the first surface 207A of the rear cover 207. The first and second connection electrodes 284-1 and 284-2 may be disposed on the rear cover 207 so as to be connected to the second and third electrodes 282 and 283, respectively. The shape of the first and second connection electrodes 284-1 and 284-2 shown in FIG. 9A is not considered as a limitation and may be variously changed. At least a portion 1010 of the first surface 207A of the rear cover 207 may be formed of a material having low transmittance so as to block internal components of the electronic device from being visible through the rear cover 207 formed of a light-transmitting material. At least a portion of the first and second connection electrodes 284-1 and 284-2 may be disposed at least in part on the portion 1010, formed of a material having low transmittance, of the first surface 207A of the rear cover 207.

Referring to FIG. 9B, the second electrode 282 substantially disposed on the second surface 207B of the rear cover 207 may include two layers 282-1 and 282-2. For example, the first layer 282-1 of the second electrode 282 may include the above-described conductive material (TiAlCrSiCN), and the second layer 282-2 may include a conductive material different from the first layer 282-1. The second layer 282-2 may be disposed between the first layer 282-1 and the second surface 207B of the rear cover 207. The second layer 282-2 that is not exposed to the outside may have a lower weight of considering durability or corrosion resistance than the first layer 282-1. The second layer 282-2 may be formed of a metal or conductive paste having excellent electrical conductivity.

The second layer 282-2 of the second electrode 282 may be extended from the second surface 207B of the rear cover 207 to at least a portion of the first surface 207A of the rear cover 207 along the outer peripheral surface of the rear cover 207. The second layer 282-2 of the second electrode 282 may then be electrically connected to the first connection electrode 284-1 disposed on the first surface 207A of the rear cover 207.

The third electrode 283 may also include two layers 283-1 and 283-2. The first and second layers 283-1 and 283-2 of the third electrode 283 may have the same arrangement as that of the first and second layers 282-1 and 282-2 of the second electrode 282.

The second layer 283-2 of the third electrode 283 may be extended from the second surface 207B of the rear cover 207 to at least a portion of the first surface 207A of the rear cover 207 along the outer peripheral surface of the rear cover 207. The second layer 283-2 of the third electrode 283 may then be electrically connected to the second connection electrode 284-2 disposed on the first surface 207A of the rear cover 207.

According to various embodiments of the present disclosure, an electronic device may include a housing, a display viewed through at least a portion of a front surface of the housing, a rear cover disposed on a rear surface of the housing, a first electrode disposed on a lateral surface of the housing, and second and third electrodes disposed at different positions on the rear cover. The first electrode, the second electrode, and the third electrode may include a conductive material that is a compound containing titanium (Ti), aluminum (Al), chromium (Cr), silicon (Si), carbon (C), and nitrogen (N).

At least one of the first electrode, the second electrode, and the third electrode may be an electrode that is in contact with a user's skin and measures an electrical signal according to a user's biological activity.

The conductive material may include titanium (Ti) of about 1 to 7% by weight, aluminum (Al) of about 1 to 7% by weight, chromium (Cr) of about 15 to 35% by weight, silicon (Si) of about 3 to 15% by weight, carbon (C) of about 8 to 25% by weight, and nitrogen (N) of about 15 to 35% by weight.

The first electrode may be formed on a button installed on the lateral surface of the housing and formed of a conductive substance.

The button may include at least a portion of a non-conductive material and at least another portion of the conductive material.

The rear cover may have a first surface facing a printed circuit board and a second surface opposite to the first surface, and the second electrode and the third electrode may be disposed substantially on the second surface of the rear cover. Also, the electronic device may further include a first connection electrode disposed substantially on the first surface of the rear cover and electrically connecting the second electrode to the printed circuit board, and a second connection electrode disposed substantially on the first surface of the rear cover and electrically connecting the third electrode to the printed circuit board.

The second electrode and the first connection electrode may be electrically connected to each other on an outer circumferential surface of the rear cover, and the third electrode and the second connection electrode may be electrically connected to each other on the outer circumferential surface of the rear cover.

The first connection electrode and the second connection electrode may include a material or conductive paste formed of chromium (Cr), titanium (Ti), gold (Au), silver (Ag), or a combination thereof.

The second electrode may include a plurality of layers having different conductive substances, and the third electrode may include a plurality of layers having different conductive substances.

Each of the second electrode and the third electrode may include a stack of a first layer having the conductive material and a second layer having a conductive substance different from the conductive material.

According to various embodiments of the present disclosure, an electrode of an electronic device may include a first electrode disposed on at least a portion of a housing of the electronic device, and second and third electrodes disposed at different positions on a rear cover disposed on a rear surface of the housing. The first electrode, the second electrode, and the third electrode may include a conductive material that is a compound containing titanium (Ti), aluminum (Al), chromium (Cr), silicon (Si), carbon (C), and nitrogen (N).

In addition, the rear cover may have a first surface facing a printed circuit board of the electronic device and a second surface opposite to the first surface, and the second electrode and the third electrode may be disposed substantially on the second surface of the rear cover. Also, the electrode may further include a first connection electrode disposed substantially on the first surface of the rear cover and electrically connecting the second electrode to the printed circuit board, and a second connection electrode disposed substantially on the first surface of the rear cover and electrically connecting the third electrode to the printed circuit board.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   a housing;
   a display viewable through at least a portion of a front surface of the housing;
   a rear cover disposed on a rear surface of the housing;
   a first electrode disposed on a lateral surface of the housing; and
   second and third electrodes disposed at different positions on the rear cover,
   wherein the first electrode, the second electrode, and the third electrode include a conductive material that is a compound containing titanium (Ti), aluminum (Al), chromium (Cr), silicon (Si), carbon (C), and nitrogen (N), and
   wherein the conductive material includes chromium (Cr) of about 15 to 35% by weight, silicon (Si) of about 3 to 15% by weight, carbon (C) of about 8 to 25% by weight, and nitrogen (N) of about 15 to 35% by weight.

2. The electronic device of claim 1, wherein at least one of the first electrode, the second electrode, and the third electrode is an electrode that is in contact with a user's skin and measures an electrical signal according to a user's biological activity.

3. The electronic device of claim 1, wherein the conductive material further includes titanium (Ti) of about 1 to 7% by weight, and aluminum (Al) of about 1 to 7% by weight.

4. The electronic device of claim 1, wherein the first electrode is formed on a button installed on the lateral surface of the housing and formed of a conductive substance.

5. The electronic device of claim 4, wherein the button includes a first portion of a non-conductive material and a second portion of the conductive material.

6. The electronic device of claim 1,
wherein the rear cover has a first surface facing a printed circuit board and a second surface opposite to the first surface,
wherein the second electrode and the third electrode are disposed substantially on the second surface of the rear cover, and
wherein the electronic device further comprises:
a first connection electrode disposed substantially on the first surface of the rear cover and electrically connecting the second electrode to the printed circuit board, and
a second connection electrode disposed substantially on the first surface of the rear cover and electrically connecting the third electrode to the printed circuit board.

7. The electronic device of claim 6,
wherein the second electrode and the first connection electrode are electrically connected to each other on an outer circumferential surface of the rear cover, and
wherein the third electrode and the second connection electrode are electrically connected to each other on the outer circumferential surface of the rear cover.

8. The electronic device of claim 6, wherein the first connection electrode and the second connection electrode include a material or conductive paste formed of chromium (Cr), titanium (Ti), gold (Au), silver (Ag), or a combination thereof.

9. The electronic device of claim 6,
wherein the second electrode includes a plurality of layers having different conductive substances, and
wherein the third electrode includes a plurality of layers having different conductive substances.

10. The electronic device of claim 6, wherein each of the second electrode and the third electrode includes a stack of a first layer having the conductive material and a second layer having a conductive substance different from the conductive material.

11. An electrode of an electronic device, comprising:
a first electrode disposed on a portion of a housing of the electronic device; and
second and third electrodes disposed at different positions on a rear cover disposed on a rear surface of the housing,
wherein the first electrode, the second electrode, and the third electrode include a conductive material that is a compound titanium (Ti), aluminum (Al), chromium (Cr), silicon (Si), carbon (C), and nitrogen (N), and
wherein the conductive material includes chromium (Cr) of about 15 to 35% by weight, silicon (Si) of about 3 to 15% by weight, carbon (C) of about 8 to 25% by weight and nitrogen (N) of about 15 to 35% by weight.

12. The electrode of claim 11, wherein at least one of the first electrode, the second electrode, and the third electrode is an electrode that is in contact with a user's skin and measures an electrical signal according to a user's biological activity.

13. The electrode of claim 11, wherein the conductive material further includes titanium (Ti) of about 1 to 7% by weight, and aluminum (Al) of about 1 to 7% by weight.

14. The electrode of claim 11, wherein the first electrode is formed on a button installed on a lateral surface of the housing and formed of a conductive substance.

15. The electrode of claim 14, wherein the button includes a first portion of a non-conductive material and a second portion of the conductive material.

16. The electrode of claim 11,
wherein the second electrode and the third electrode are disposed substantially on a second surface of a rear cover of the electronic device, and
wherein the electrode further comprises:
a first connection electrode disposed substantially on a first surface of the rear cover opposite the second surface and electrically connecting the second electrode to a printed circuit board facing the first surface, and
a second connection electrode disposed substantially on the first surface of the rear cover and electrically connecting the third electrode to the printed circuit board.

17. The electrode of claim 16, wherein the first connection electrode and the second connection electrode include a material or conductive paste formed of chromium (Cr), titanium (Ti), gold (Au), silver (Ag), or a combination thereof.

18. The electrode of claim 16,
wherein the second electrode includes a plurality of layers having different conductive substances, and
wherein the third electrode includes a plurality of layers having different conductive substances.

19. The electrode of claim 16, wherein each of the second electrode and the third electrode includes a stack of a first layer having the conductive material and a second layer having a conductive substance different from the conductive material.

20. The electrode of claim 16, wherein respective compositions of the first electrode, the second electrode, and the third electrode are selected according to a position on the electronic device where each electrode is disposed.

* * * * *